United States Patent
Rigassi-Dietrich et al.

(10) Patent No.: US 8,617,595 B2
(45) Date of Patent: *Dec. 31, 2013

(54) GALENIC FORMULATIONS OF ORGANIC COMPOUNDS

(75) Inventors: Petra G Rigassi-Dietrich, Therwil (CH); Martin Schmid, Wettingen (CH)

(73) Assignee: Novartis AG, Basel (CH)

( * ) Notice: Subject to any disclaimer, the term of this patent is extended or adjusted under 35 U.S.C. 154(b) by 340 days.

This patent is subject to a terminal disclaimer.

(21) Appl. No.: 10/590,398

(22) PCT Filed: Mar. 16, 2005

(86) PCT No.: PCT/EP2005/002798
§ 371 (c)(1),
(2), (4) Date: Aug. 23, 2006

(87) PCT Pub. No.: WO2005/089729
PCT Pub. Date: Sep. 29, 2005

(65) Prior Publication Data
US 2007/0197655 A1 Aug. 23, 2007

Related U.S. Application Data

(60) Provisional application No. 60/553,878, filed on Mar. 17, 2004.

(51) Int. Cl.
*A61K 9/20* (2006.01)
(52) U.S. Cl.
USPC .......................................... 424/464; 514/616
(58) Field of Classification Search
USPC .......................................................... 424/464
See application file for complete search history.

(56) References Cited

U.S. PATENT DOCUMENTS 3,039,922 A * 6/1962 Berger et al. ................. 514/357
2001/0044472 A1* 11/2001 Upadhyay et al. ............ 514/629
2003/0114389 A1* 6/2003 Webb .............................. 514/19

FOREIGN PATENT DOCUMENTS

| EP | 1 312 379 A1 | 5/2003 |
| WO | 02/40007 A1 | 5/2002 |
| WO | WO 03/035046 | 5/2003 |
| WO | WO 2004/002466 | 1/2004 |

OTHER PUBLICATIONS

Drug Factsheets (http://chealth.canoe.ca/drug_info_details.asp?brand_name_id =4983&rot=4).*
http://www.aerosil.com/product/aerosil/en/industries/application-areas/pharmaceuticals/solid-drug-forms/pages/default.aspx).
AEROSIL ® colloidal silicon dioxide for solid dosage forms Jul. 2012 colloidal silicon dioxide for solid dosage forms.
Remington's Pharmaceutical Sciences, 1605 (Mack Publishing Company 1985).
Drug Factsheets (http://chealth.canoe.ca/drug_info_details.asp?brand_name_id =4983&rot=4), downloaded on Jan. 10, 2012.
"Starch" In: Rowe, R.C.; Sheskey, P.J.; Weller, P.J.: "Handbook of Pharmaceutical Excipients, 4th edition", 2003, Pharmaceutical Press, London, pp. 603-608.
Arthur H Kibbe Ed—Kibbe A H (ED): 11Povidoneu, Jan. 1, 2000, Handbook of Pharmaceutical Excipients, American Pharmaceutical Assoc. [U.A.], Washington DC; US, pp. 433-439, XP002465530, ISBN: 978-0-85369-381-9.

* cited by examiner

*Primary Examiner* — Jake Vu
(74) *Attorney, Agent, or Firm* — Jim Lynch

(57) ABSTRACT

The present invention relates to a solid oral dosage form comprising a therapeutically effective amount of aliskiren or a pharmaceutically acceptable salt thereof, and wherein the active ingredient is present in an amount of more than 46% by weight based on the total weight of the oral dosage form.

20 Claims, No Drawings

GALENIC FORMULATIONS OF ORGANIC COMPOUNDS

This application claims benefit of U.S. Provisional Application 60/553,878, filed Mar. 17, 2004.

The present invention relates to solid oral dosage forms comprising an orally active renin inhibitor, aliskiren, or a pharmaceutically acceptable salt thereof, as the active ingredient in a suitable carrier medium. In particular, the present invention provides galenic formulations comprising aliskiren, preferably, a hemi-fumarate salt thereof, alone or in combination with another active agent. The present invention also relates to the processes for their preparation and to their use as medicaments.

In the following the term "aliskiren", if not defined specifically, is to be understood both as the free base and as a salt thereof, especially a pharmaceutically acceptable salt thereof, most preferably a hemi-fumarate thereof.

Renin released from the kidneys cleaves angiotensinogen in the circulation to form the decapeptide angiotensin I. This is in turn cleaved by angiotensin converting enzyme in the lungs, kidneys and other organs to form the octapeptide angiotensin II. The octapeptide increases blood pressure both directly by arterial vasoconstriction and indirectly by liberating from the adrenal glands the sodium-ion-retaining hormone aldosterone, accompanied by an increase in extracellular fluid volume. Inhibitors of the enzymatic activity of renin bring about a reduction in the formation of angiotensin I. As a result a smaller amount of angiotensin II is produced. The reduced concentration of that active peptide hormone is the direct cause of, e.g., the antihypertensive effect of renin inhibitors. Accordingly, renin inhibitors, or salts thereof, may be employed, e.g., as antihypertensives or for treating congestive heart failure.

The renin inhibitor, aliskiren, in particular, a hemi-fumarate thereof, is known to be effective in the treatment of reducing blood pressure irrespective of age, sex or race and is also well tolerated. Aliskiren in form of the free base is represented by the following formula

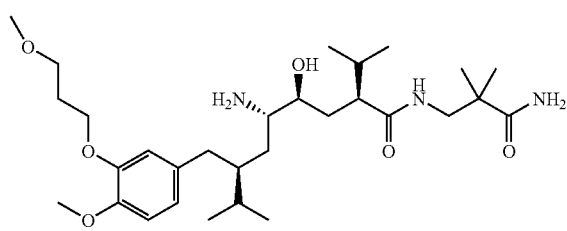

(I)

and chemically defined as 2(S),4(S),5(S),7(S)—N-(3-amino-2,2-dimethyl-3-oxopropyl)-2,7-di(1-methylethyl)-4-hydroxy-5-amino-8-[4-methoxy-3-(3-methoxy-propoxy)phenyl]-octanamide. As described above, most preferred is the hemi-fumarate salt thereof which is specifically disclosed in EP 678503 A as Example 83.

The oral administration of such pharmaceutical agents as tablets or capsules has certain advantages over parenteral administration such as i.v. or i.m. Diseases requiring treatment with painful injectable formulations are considered to be more serious than those conditions which can be treated with oral dosage forms. However, the major advantage with oral formulations is held to be their suitability for self administration whereas parenteral formulations have to be administered in most cases by a physician or paramedical personnel.

However, aliskiren is difficult to formulate and heretofore it has not been possible to make oral formulations in the form of tablets in a reliable and robust way. In a galenic formulation comprising aliskiren, or a pharmaceutically acceptable salt thereof, a high amount is normally heeded of the drug substance (DS) with properties that make the formulation of tablets difficult.

For example, aliskiren has a needle shaped crystal habit, which has a negative influence on the bulk properties of the drug substance, e.g., flow properties and bulk density. The compression behavior of the drug substance is poor, leading to weak interparticulate bonds and polymorphism changes under pressure. Aliskiren has a strong elastic component that also leads to weakening of interparticulate bonds. The high dose (up to 300 or 600 mg of the free base per tablet) makes a high drug loading necessary in order to achieve a reasonable tablet size.

The drug substance quality is very variable with effect on the processability of a tablet, e.g., particle size distribution, bulk density, flowability, wetting behavior, surface area and sticking tendency. Moreover, aliskiren is highly hygroscopic. In contact with water, the drug substance polymorphism changes to an amorphous state, which shows inferior stability compared to the crystalline state. The combination of these hurdles makes a standard tablet manufacturing process extremely difficult.

Direct compression is not a feasible option for routine production because of, e.g., the high hygroscopicity, the needle shaped particle structure, the poor flowability with resulting processability problems and dose uniformity problems. A roller compaction process leads to a reduction of the high bulk volume of the drug substance. Yet, the pre-compression of the drug substance during roller compaction makes a further compression into tablets with sufficient hardness and resistance to friability without a high amount of excipients extremely difficult due to the low compressibility of the drug substance. A tablet with a drug load of aliskiren higher than ca. 35% has been found not to lead to robust tablets (e.g. friability, hardness) and a robust process (e.g. sticking and picking during roller compaction and tabletting).

Accordingly, a suitable and robust galenic formulation overcoming the above problems relating to the properties of aliskiren need to be developed.

The present invention has solved the above problems resulting in a robust formulation avoiding all the above disadvantages and in a process suitable for large-scale manufacture of solid oral dosage forms.

The present invention relates to a solid oral dosage form comprising a therapeutically effective amount of aliskiren, or a pharmaceutically acceptable salt thereof, and wherein the active ingredient is present in an amount of more than 46% by weight based on the total weight of the oral dosage form, either dependent on or not dependent on any coating or capsule material used.

If not dependent on any coating or capsule used, the active ingredient is present in an amount of more than 48% by weight based on the total weight of the oral dosage form. If dependent on any coating or capsule used, the active ingredient is present in an amount of more than 46% by weight based on the total weight of the oral dosage form.

In a preferred embodiment of the present invention, the active agent is present in an amount ranging from 46 to 60% by weight based on the total weight of the oral dosage form.

In another preferred embodiment of the present invention, the active agent is present in an amount of more than 46% up to 56% by weight based on the total weight of the oral dosage form.

In a solid oral dosage form according to the present invention wherein the active agent consists entirely of aliskiren, or a pharmaceutically acceptable salt thereof, it is preferred if the active agent is present in an amount ranging from about 75 mg to about 600 mg of the free base per unit dosage form.

In a preferred embodiment of the present invention, the active agent consists entirely of aliskiren, or a pharmaceutically acceptable salt thereof, and is present in an amount ranging from about 75 to about 300 mg of the free base per unit dosage form.

In a further preferred embodiment of the present invention, the dosage of aliskiren is in the form of a hemi-fumarate thereof and is present in an amount of about 83, about 166, about 332 or about 663 mg per unit dosage form.

Solid oral dosage forms according to the present invention provide for the administration of the active ingredient in a smaller oral form than was heretofore possible for a given unit dose of the active agent. Furthermore, the oral dosage forms obtained are stable both to the production process and during storage, e.g., for about 2 years in conventional packaging, e.g., sealed aluminium blister packs.

The terms "effective amount" or "therapeutically effective amount" refers to the amount of the active ingredient or agent which halts or reduces the progress of the condition being treated or which otherwise completely or partly cures or acts palliatively on the condition.

Aliskiren, or a pharmaceutically acceptable salt thereof, can, e.g., be prepared in a manner known per se, especially as described in EP 678503 A, e.g., in Example 83.

A solid oral dosage form comprises a capsule or more preferably a tablet or a film-coated tablet.

A solid oral dosage form according to the invention comprises additives or excipients that are suitable for the preparation of the solid oral dosage form according to the present invention. Tabletting aids, commonly used in tablet formulation can be used and reference is made to the extensive literature on the subject, see in particular Fiedler's "Lexicon der Hilfstoffe", 4th Edition, ECV Aulendorf 1996, which is incorporated herein by reference. These include, but are not limited to, fillers, binders, disintegrants, lubricants, glidants, stabilising agents, fillers or diluents, surfactants, film-formers, softeners, pigments and the like.

In a preferred embodiment the solid oral dosage form according to the present invention comprises as an additive a filler.

In a preferred embodiment the solid oral dosage form according to the present invention comprises as an additive, in addition to a filler, a disintegrant.

In a preferred embodiment the solid oral dosage form according to the present invention comprises as an additive, in addition to a filler and a disintegrant, a lubricant.

In a preferred embodiment the solid oral dosage form according to the present invention comprises as an additive, in addition to a filler, a disintegrant and a lubricant, a glidant.

In a preferred embodiment the solid oral dosage form according to the present invention comprises as an additive, in addition to a filler, a disintegrant, a lubricant and a glidant, a binder.

As fillers one can particularly mention starches, e.g., potato starch, wheat starch, corn starch, hydroxypropyl cellulose, hydroxyethyl cellulose, hydroxypropyl methyl cellulose (HPMC) and, preferably, microcrystalline cellulose, e.g., products available under the registered trade marks AVICEL, FILTRAK, HEWETEN or PHARMACEL.

As binders for wet granulation, one can particularly mention polyvinylpyrrolidones (PVP), e.g., PVP K 30, HPMC, e.g., viscosity grades 3 or 6 cps, and polyethylene glycols (PEG), e.g., PEG 4000. A most preferred binder is PVP K 30.

As disintegrants one can particularly mention carboxymethylcellulose calcium (CMC-Ca), carboxymethylcellulose sodium (CMC-Na), crosslinked PVP (e.g. CROSPOVIDONE, POLYPLASDONE or KOLLIDON XL), alginic acid, sodium alginate and guar gum, most preferably crosslinked PVP (CROSPOVIDONE), crosslinked CMC (Ac-Di-Sol), carboxymethylstarch-Na (PIRIMOJEL and EXPLOTAB). A most preferred disintegrant is CROSPOVIDONE.

As glidants one can mention in particular colloidal silica, such as colloidal silicon dioxide, e.g., AEROSIL, magnesium (Mg) trisilicate, powdered cellulose, starch, talc and tribasic calcium phosphate or combinations of these with fillers or binders, e.g., silicified microcrystalline cellulose (PROSOLV). A most preferred glidant is colloidal silicon dioxide (e.g. AEROSIL 200).

As fillers or diluents one can mention confectioner's sugar, compressible sugar, dextrates, dextrin, dextrose, lactose, mannitol, microcrystalline cellulose, in particular, having a density of about $0.45$ g/cm$^3$, e.g., AVICEL, powdered cellulose, sorbitol, sucrose and talc. A most preferred filler is microcrystalline cellulose.

As lubricants one can mention in particular Mg stearate, aluminum (Al) or Ca stearate, PEG 4000 to 8000 and talc, hydrogenated castor oil, stearic acid and salts thereof, glycerol esters, Na-stearylfumarate, hydrogenated cotton seed oil and others. A most preferred lubricant is Mg stearate.

Additives to be used as filmcoating materials comprise polymers such as HPMC, PEG, PVP, polyvinylpyrrolidone-vinyl acetate copolymer (PVP-VA), polyvinyl alcohol (PVA), and sugar as film formers. A most preferred coating material is HPMC, especially HPMC 3 cps (preferred amount 5-6 mg/cm$^2$), and mixtures thereof with further additives, e.g., those available under the registered trade mark OPADRY. Further additives comprise pigments, dies, lakes, most preferred TiO$_2$ and iron oxides, anti-tacking agents like talk and softeners like PEG 3350, 4000, 6000, 8000 or others. Most preferred additives are talk and PEG 4000.

The present invention likewise relates to a solid oral dosage form comprising a therapeutically effective amount of aliskiren, or a pharmaceutically acceptable salt thereof, as an active agent, and a filler as an additive. Further additives include, but are not limited to, binders, disintegrants, lubricants, glidants, stabilising agents, diluents, surfactants, film formers, pigments, softeners and antitacking agents and the like. The amounts of the active ingredient and further additives are preferably those as defined above.

The present invention likewise relates to a solid oral dosage form comprising a therapeutically effective amount of aliskiren, or a pharmaceutically acceptable salt thereof, as an active agent, and a filler and a disintegrant as additives. Further additives include, but are not limited to, binders, lubricants, glidants, stabilising agents, diluents, surfactants, film formers, pigments, softeners and antitacking agents and the like. The amounts of the active ingredient and further additives are preferably those as defined herein above.

The present invention likewise relates to a solid oral dosage form comprising a therapeutically effective amount of aliskiren, or a pharmaceutically acceptable salt thereof, as an active agent, and a filler, a disintegrant and a lubricant as additives. Further additives include, but are not limited to, binders, glidants, stabilising agents, diluents, surfactants, film formers, pigments, softeners and antitacking agents and the like. The amounts of the active ingredient and further additives are preferably those as defined herein above.

The present invention likewise relates to a solid oral dosage form comprising a therapeutically effective amount of aliskiren, or a pharmaceutically acceptable salt thereof, as an active agent, and a filler, a disintegrant, a lubricant and a glidant as additives. Further additives include, but are not limited to, binders, stabilising agents, diluents, surfactants, film formers, pigments, softeners and antitacking agents and the like. The amounts of the active ingredient and further additives are preferably those as defined herein above.

The present invention likewise relates to a solid oral dosage form comprising a therapeutically effective amount of aliskiren, or a pharmaceutically acceptable salt thereof, as an active agent, and a filler, a disintegrant, a lubricant, a glidant and a binder as additives. Further additives include, but are not limited to, stabilising agents, diluents, surfactants, film formers, pigments, softeners and antitacking agents and the like. The amounts of the active ingredient and further additives are preferably those as defined herein above.

One or more of these additives can be selected and used by a person skilled in the art having regard to the particular desired properties of the solid oral dosage form by routine experimentation and without any undue burden.

The amount of each type of additive employed, e.g., glidant, binder, disintegrant, filler or diluent and lubricant or film coat may vary within ranges conventional in the art. Thus, for example, the amount of lubricant may vary within a range of from 0.2 to 5% by weight, in particular, for Mg stearate from 0.5 to 2.0% by weight, e.g., from 0.8 to 1.5% by weight; the amount of binder may vary within a range of from 0 to about 20% by weight, e.g., from 3 to 4% by weight; the amount of disintegrant may vary within a range of from 0 to about 20% by weight, e.g., from 13.5 to 16% by weight; the amount of filler or diluent may vary within a range of from 0 to about 80% by weight, e.g., from 20 to 32% by weight; whereas the amount of glidant may vary within a range of from 0 to about 5% by weight, e.g. from 0.4 to 0.6% by weight; and the amount of film coat may vary within a range of 0 to 20 mg/cm$^2$, e.g. 4 to 7 mg/cm$^2$.

It is a characteristic of the present solid oral dosage forms that they contain only a relatively small amount of additives given the high content of the active agent. This enables the production of physically small unit dosage forms. The total amount of additives in a given uncoated unit dosage may be about 60% or less by weight based on the total weight of the solid oral dosage form, more particularly about 54% or less. Preferably, the additive content is in the range of about 35 to 55% by weight, more particularly, the additive content ranges from about 50 to about 52% by weight.

A preferred amount of a filler, especially of microcrystalline cellulose, ranges from about 20 to 32% by weight per unit dosage form.

A preferred amount of a binder, especially of PVP K 30, ranges from about 3 to 4% by weight per unit dosage form.

A preferred amount of a disintegrant, especially of CROSPOVIDONE, ranges from about 13.5 to 15% by weight per unit dosage form.

A preferred amount of a glidant, especially of colloidal silicon dioxide, ranges from about 0.4 to 0.6% by weight per unit dosage form.

A preferred amount of a lubricant, especially of Mg stearate, ranges from about 0.8 to 1.5% by weight per unit dosage form.

A preferred amount of a film coat, especially of HPMC 3 cps, ranges from about 4 to 7 mg/cm$^2$ per unit dosage form.

Preferred amounts of aliskiren and additives are further shown in the illustrative Examples.

The absolute amounts of each additive and the amounts relative to other additives is similarly dependent on the desired properties of the solid oral dosage form and may also be chosen by the skilled artisan by routine experimentation without undue burden. For example, the solid oral dosage form may be chosen to exhibit accelerated and/or delayed release of the active agent with or without quantitative control of the release of active agent.

Thus, where accelerated release is desired a disintegrant such as crosslinked PVP, e.g., those products available under the registered trade marks POLYPLASDONE XL or KOLLIDON CL, in particular, having a molecular weight in excess of 1,000,000, more particularly, having a particle size distribution of less than 400 microns or, preferably, less than 74 microns, or comprising reactive additives (effervescent mixtures) that effect rapid disintegration of the tablet in the presence of water, for example so-called effervescent tablets that contain an acid in solid form, typically citric acid, which acts in water on a base containing chemically combined carbon dioxide, for example sodium hydrogencarbonate or sodium carbonate, and releases carbon dioxide.

Whereas if delayed release is desired one may employ coating technology for multiparticulates (e.g. pellets, minitablets), wax matrix systems, polymer matrix tablets or polymer coatings or other technologies conventional in the art.

Quantitative control of the release of the active agent can be achieved by conventional techniques known in the art. Such dosage forms are known as oral osmotic systems (e.g. OROS), coated tablets, matrix tablets, press-coated tablets, multilayer tablets and the like.

In a solid oral dosage form wherein the active agent consists entirely of aliskiren, or a pharmaceutically acceptable salt thereof, or a combination of aliskiren with other active pharmaceutical ingredients, preferred additives are microcrystalline cellulose, hydroxypropylcellulose, crosslinked PVP, PVP, PEG, CMC-Na or CMC-Ca, Mg stearate, Ca stearate or Al stearate, anhydrous colloidal silica, talc, titanium dioxide and iron oxide pigments. The amounts of additive employed will depend upon how much active agent is to be used. The stearate, e.g., Mg stearate is preferably employed in amounts of 0.8 to 1.5% by weight. Whereas the silica is preferably employed in an amount of from 0.4 to 0.6% by weight.

The amount of aliskiren in the form of the hemi-fumarate thereof within the total weight of the uncoated unit dosage form ranges, preferably, from about 83 to about 663 mg, most preferably, the amount of aliskiren hemi-fumarate is about 83, about 166 or about 332 mg per unit dosage form.

The amount of the binder within the total weight of the uncoated unit dosage form is preferably from 2 to 5%, most preferably from 3 to 4% by weight per unit dosage form.

The amount of the disintegrant within total weight of the uncoated unit dosage form is preferably from 0 to 20%, most preferably from 13.5 to 16% by weight per unit dosage form.

The amount of the glidant within the total weight of the uncoated unit dosage form is preferably from 0 to 5%, most preferably from 0.4 to 0.6% by weight per unit dosage form.

The amount of the lubricant within the total weight of the uncoated unit dosage form is preferably from 0.2 to 5%, most preferably from 0.8 to 1.5% for Mg stearate by weight per unit dosage form.

A preferred amount of a film coat, especially of HPMC 3 cps, is from about 4 to about 7 mg/cm$^2$ per unit dosage form.

The weight ratio of aliskiren to the binder preferably ranges from about 8:1 to about 25:1, more preferably from about 11:1 to about 15:1. Most preferably, the weight ratio is about 12.5:1.

The weight ratio of aliskiren to the disintegrant preferably ranges from about 2:1 to about 4:1, more preferably from about 2.5:1 to about 3.7:1. Most preferably, the weight ratio is about 3.1:1.

The weight ratio of aliskiren to the glidant preferably ranges from about 75:1 to about 125:1, more preferably from about 80:1 to about 90:1. Most preferably, the weight ratio is about 83.3:1.

The weight ratio of aliskiren to the lubricant preferably ranges from about 25:1 to about 63:1, more preferably from about 30:1 to about 50:1. Most preferably, the weight ratio is about 30:1.

The solid oral dosage forms according to the present invention may also be in the form of film-coated tablets or dragées in which case the solid oral dosage form is provided with a coating typically a polymer like HPMC, PVP or the like, sugar, shellac or other film-coating entirely conventional in the art. Attention is drawn to the numerous known methods of coating employed in the art, e.g., spray coating in a fluidized bed, e.g., by the known methods using apparatus available from Aeromatic, Glatt, Wurster or Hüttlin, in a perforated pan coater, e.g., by the known methods using apparatus from Accela Cota, Glatt, Driam or others, or other methods conventional in the art. The additives commonly used in confectioning may be employed in such methods.

A further embodiment of the present invention is a process for the manufacture of a solid oral dosage form according to the present invention.

Wet granulation of aliskiren with excipients using water and/or an aqueous binder solution leads to a change in polymorphism of the drug substance which changes partly to the amorphous state and causes an inferior chemical stability of the drug product (DP).

However, wet granulation of aliskiren using a mixture of organic solvents or an organic binder solution has been found to be the best way of manufacturing suitable aliskiren solid oral dosage forms, especially tablets, showing following advantages:

Said wet granulation reduces the bulk volume of aliskiren during granulation;
The influences of a changing drug substance quality are minimized;
A high drug loading above 46% by weight per unit dosage form may easily be achieved;
The formulation of tablets with sufficient hardness, resistance to friability, disintegration time, dissolution rate etc. is possible;
The sticking tendency and poor flow of the drug substance is reduced to a minimum;
A robust manufacturing process of the DP is achieved;
Scale-up of formulation and process resulting in a reproducible DP performance is achieved; and
Sufficient stability to achieve a reasonable shelf life is achieved.

The excipients may be distributed partly in the inner (granular) phase and partly in the outer phase, which is the case in the described invention. Microcrystalline cellulose (filler) and CROSPOVIDONE (disintegrant) are partly in the inner and partly in the outer phase, PVP K 30 (binder) is only part of the inner phase, being the binder during granulation, whereas colloidal silicon dioxide (glidant) and Mg stearate (lubricant) are only part of the outer phase.

The inner phase excipients, e.g., filler, binder and disintegrant, and the drug substance are mixed and granulated with an ethanolic solution of the binder and additional ethanol. The granulate is dried and sieved. The outer phase containing, e.g., disintegrant, filler, glidant and lubricant, is screened with the dried granulate and mixed. The mixture is compressed into tablets. The cores may optionally be coated with a film-coat.

The granulate phase is defined as the inner phase, the excipients added to the granulate are defined as the outer phase of the tabletting mixture.

The invention likewise relates to a process for the preparation of solid oral dosage forms as described herein above. Such solid oral dosage form may be produced by working up components as defined herein above in the appropriate amounts, to form unit dosage forms.

Accordingly, the present invention provides a process for the manufacture of a solid oral dosage form of the present invention comprising:
1) mixing the active ingredient and additives and granulating said components with a granulation liquid;
2) drying a resulting granulate;
3) mixing the dried granulate with outer phase excipients;
4) compressing a resulting mixture to form a solid oral dosage as a core tablet; and
5) optionally coating a resulting core tablet to give a film-coated tablet.

Preferably, the additives in step (1) are selected from a filler, a disintegrant and a binder; and the outer phase excipients in step (3) are selected from a filler, a disintegrant, a lubricant and a glidant.

The granulation liquid can be ethanol, a mixture of ethanol and water, a mixture of ethanol, water and isopropanol, or a solution of PVP in the before mentioned mixtures. A preferred mixture of ethanol and water ranges from about 50/50 to about 99/1 (% w/w), most preferrably it is about 94/6 (% w/w). A preferred mixture of ethanol, water and isopropanol ranges from about 45/45/5 to about 98/1/1 (% w/w/w), most preferably from about 88.5/5.5/6.0 to about 91.5/4.5/4.0 (% w/w/w). A preferred concentration of PVP in the above named mixtures ranges from about 5 to about 30% by weight, preferably from about 15 to about 25%, more preferably from about 16 to about 22%.

Attention is drawn to the numerous known methods of granulating, drying and mixing employed in the art, e.g., spray granulation in a fluidized bed, wet granulation in a high-shear mixer, melt granulation, drying in a fluidized-bed dryer, mixing in a free-fall or tumble blender, compressing into tablets on a single-punch or rotary tablet press.

The manufacturing of the granulate can be performed on standard equipment suitable for organic granulation processes. The manufacturing of the final blend and the compression of tablets can also be performed on standard equipment.

For example, step (1) may be carried out by a high-shear granulator, e.g., Collette Gral; step (2) may be conducted in a fluid-bed dryer; step (3) may be carried out by a free-fall mixer (e.g. container blender, tumble blender); and step (4) may be carried out using a dry compression method, e.g., a rotary tablet press.

As described above, the core tablets may then be optionally film-coated.

Due to the high hygroscopicity and water sensitivity of aliskiren with respect to changes in polymorphism, the use of water has preferably to be avoided in order to prevent the drug substance from changes in polymorphism for the above stated reasons (amorphous state, inferior chemical stability). A solution for said problem is to apply an organic film-coating process.

Surprisingly it was found that an aqueous film coating process using a standard film-coat composition can be applied to aliskiren core tablets without changes in polymorphism.

The film-coat preferably consists of HPMC as the polymer, iron oxide pigments, titanium dioxide as coloring agent, PEG as softener and talc as anti-tacking agent. The use of coloring agents or dyes may serve to enhance the appearance as well as to identify the compositions. Other dyes suitable for use typically include carotinoids, chlorophyll and lakes.

The film coating conditions have to assure that the tablet cores do not take up considerable amounts of moisture and that the drug substance within the tablets does not closely get into contact with water droplets. This is achieved by process parameter settings that reduce the amount of humidity which gets onto the tablet cores.

The solid oral dosage forms of the present invention are useful for lowering the blood pressure, either systolic or diastolic or both. The conditions for which the instant invention is useful include, without limitation, hypertension (whether of the malignant, essential, reno-vascular, diabetic, isolated systolic, or other secondary type), congestive heart failure, angina (whether stable or unstable), myocardial infarction, artherosclerosis, diabetic nephropathy, diabetic cardiac myopathy, renal insufficiency, peripheral vascular disease, left ventricular hypertrophy, cognitive dysfunction (such as Alzheimer's) and stroke, headache and chronic heart failure.

The present invention likewise relates to a method of treating hypertension (whether of the malignant, essential, reno-vascular, diabetic, isolated systolic, or other secondary type), congestive heart failure, angina (whether stable or unstable), myocardial infarction, artherosclerosis, diabetic nephropathy, diabetic cardiac myopathy, renal insufficiency, peripheral vascular disease, left ventricular hypertrophy, cognitive dysfunction, e.g., Alzheimer's, stroke, headache and chronic heart failure comprising administering to an animal, including human patient, in need of such treatment a therapeutically effective solid oral dosage form according to the present invention.

The present invention likewise relates to the use of a solid oral dosage form according to the present invention for the manufacture of a medicament for the treatment of hypertension (whether of the malignant, essential, reno-vascular, diabetic, isolated systolic, or other secondary type), congestive heart failure, angina (whether stable or unstable), myocardial infarction, artherosclerosis, diabetic nephropathy, diabetic cardiac myopathy, renal insufficiency, peripheral vascular disease, left ventricular hypertrophy, cognitive dysfunction, e.g., Alzheimer's, stroke, headache and chronic heart failure.

The present invention likewise relates to a pharmaceutical composition for the treatment of hypertension (whether of the malignant, essential, reno-vascular, diabetic, isolated systolic, or other secondary type), congestive heart failure, angina (whether stable or unstable), myocardial infarction, artherosclerosis, diabetic nephropathy, diabetic cardiac myopathy, renal insufficiency, peripheral vascular disease, left ventricular hypertrophy, cognitive dysfunction, e.g., Alzheimer's, stroke, headache and chronic heart failure, comprising a solid oral dosage form according to the present invention.

Ultimately, the exact dose of the active agent and the particular formulation to be administered depend on a number of factors, e.g., the condition to be treated, the desired duration of the treatment and the rate of release of the active agent. For example, the amount of the active agent required and the release rate thereof may be determined on the basis of known in vitro or in vivo techniques, determining how long a particular active agent concentration in the blood plasma remains at an acceptable level for a therapeutic effect.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the Examples herein are to be construed as merely illustrative and not a limitation of the scope of the present invention in any way.

Example 1

Composition of aliskiren 150 mg (free base) uncoated tablets in mg/unit.

| Component | Roller compacted tablet | Dosage form 1 | Dosage form 2 | Dosage form 3 |
|---|---|---|---|---|
| Aliskiren hemi-fumarate | 165.750 | 165.750 | 165.750 | 165.750 |
| Microcrystalline cellulose | 220.650 | 84.750 | 72.250 | 107.250 |
| Polyvinylpyrrolidon K 30 | — | — | 12.000 | 12.000 |
| Crospovidone | 84.000 | 45.000 | 44.000 | 48.200 |
| Aerosil 200 | 4.800 | 1.500 | 1.500 | 1.800 |
| Magnesium stearate | 4.800 | 3.000 | 4.500 | 5.000 |
| Total weight | 480.000 | 300.000 | 300.000 | 340.000 |

Composition of aliskiren 150 mg (free base) uncoated tablets in % by weight.

| Component | Roller compacted tablet | Dosage form 1 | Dosage form 2 | Dosage form 3 |
|---|---|---|---|---|
| Aliskiren hemi-fumarate | 34.53 | 55.25 | 55.25 | 48.75 |
| Microcrystalline cellulose | 45.97 | 28.25 | 24.08 | 31.545 |
| Polyvinylpyrrolidon K 30 | — | — | 4 | 3.53 |
| Crospovidone | 17.5 | 15 | 14.67 | 14.175 |
| Aerosil 200 | 1 | 0.5 | 0.5 | 0.53 |
| Magnesium stearate | 1 | 1 | 1.5 | 1.47 |
| Total % | 100.00 | 100.00 | 100.00 | 100.00 |

Composition of aliskiren 150 mg (free base) uncoated tablets in mg/unit (divided into inner/outer phase).

| | Component | Roller compacted tablet | Dosage form 1 | Dosage form 2 | Dosage form 3 |
|---|---|---|---|---|---|
| Inner Phase | Aliskiren hemi-fumarate | 165.75 | 165.75 | 165.75 | 165.75 |
| | Microcrystalline cellulose | 220.65 | 84.75 | 72.25 | 90.25 |
| | Polyvinylpyrrolidon K 30 | — | — | 12.00 | 12.00 |
| | Crospovidone | 36.00 | — | — | 14.20 |
| | Aerosil 200 | — | — | — | — |
| | Magnesium stearate | 2.40 | — | — | — |
| Outer phase | Crospovidone | 48.00 | 45.00 | 44.00 | 34.00 |
| | Microcrystalline cellulose | — | — | — | 17.00 |
| | Aerosil 200 | 4.80 | 1.50 | 1.50 | 1.80 |
| | Magnesium stearate | 2.40 | 3.00 | 4.50 | 5.00 |
| | Total weight | 480.00 | 300.00 | 300.00 | 340.00 |

Composition of aliskiren 150 mg (free base) uncoated tablets in % by weight (divided into inner/outer phase).

|  | Component | Roller compacted tablet | Dosage form 1 | Dosag form 2 | Dosage form 3 |
|---|---|---|---|---|---|
| Inner Phase | Aliskiren hemi-fumarate | 34.53 | 55.25 | 55.25 | 48.75 |
|  | Microcrystalline cellulose | 45.97 | 28.25 | 24.08 | 26.545 |
|  | Polyvinylpyrrolidon K 30 | — | — | 4 | 3.530 |
|  | Crospovidone | 7.5 | — | — | 4.175 |
|  | Aerosil 200 | — | — | — | — |
|  | Magnesium stearate | 0.5 | — | — | — |
| Outer phase | Crospovidone | 10 | 15 | 14.67 | 10 |
|  | Microcrystalline cellulose | — | — | — | 5 |
|  | Aerosil 200 | 1 | 0.5 | 0.5 | 0.53 |
|  | Magnesium stearate | 0.5 | 1 | 1.5 | 1.47 |
|  | Total % | 100.00 | 100.00 | 100.00 | 100.00 |

Example 2

Composition of aliskiren (dosage form 3) film-coated tablets in mg/unit.

| Component | Dosage form 3/Strength | | |
|---|---|---|---|
|  | 75 mg (free base) | 150 mg (free base) | 300 mg (free base) |
| Aliskiren hemi-fumarate | 82.875 | 165.750 | 331.500 |
| Microcrystalline cellulose | 53.625 | 107.250 | 214.500 |
| Polyvinylpyrrolidon K 30 | 6.000 | 12.000 | 24.000 |
| Crospovidone | 24.100 | 48.200 | 96.400 |
| Aerosil 200 | 0.900 | 1.800 | 3.600 |
| Magnesium stearate | 2.500 | 5.000 | 10.000 |
| Total tablet weight | 170.000 | 340.000 | 680.000 |
| Opadry premix white | 9.946 | 16.711 | 23.9616 |
| Opadry premix red | 0.024 | 0.238 | 1.8382 |
| Opadry premix black | 0.030 | 0.051 | 0.2002 |
| Total fim-coated tablet weight | 180.000 | 357.000 | 706.000 |

What is claimed is:

1. A solid oral dosage form comprising a therapeutically effective amount of aliskiren, or a pharmaceutically acceptable salt thereof, in an amount of more than 46% by weight based on the total weight of the oral dosage form, wherein the oral dosage form is in the form of a tablet and comprises a) an inner phase which is comprising aliskiren or a pharmaceutically acceptable salt thereof, microcrystalline cellulose, polyvinylpyrrolidone, and crosslinked polyvinylpyrrolidone, and b) an outer phase which is comprising crosslinked polyvinylpyrrolidone, microcrystalline cellulose, colloidal silicon dioxide, and magnesium stearate and wherein the amount of microcrystalline cellulose in the dosage form ranges from 20 to 32% by weight, the amount of crosslinked polyvinylpyrrolidone in the dosage form ranges from 13.5 to 16% by weight, the amount of polyvinylpyrrolidone in the dosage form ranges from 3 to 4% by weight, the amount of colloidal silicon dioxide in the dosage form ranges from 0.4 to 0.6% by weight, and the amount of magnesium stearate in the dosage form ranges from 0.2 up to 5% by weight.

2. The solid oral dosage form according to claim 1, wherein the tablet further comprises a film coat wherein said film coat comprises a filmcoating material selected from hydroxypropyl methyl cellulose, polyethylene glycols, polyvinylpyrrolidones, polyvinylpyrrolidone-vinyl acetate copolymer, polyvinyl alcohol, and sugar.

3. The solid oral dosage form according to claim 1, wherein the tablet is chosen from a tablet in the form of multiparticulates, multiparticulate pellets, multiparticulate minitablets, wax matrix systems, polymer matrix tablets, polymer coated tablets, oral osmotic systems, coated tablets, matrix tablets, press-coated tablets, and multilayer tablets.

4. A solid oral dosage form according to claim 1, wherein the active ingredient is present in an amount of more than 48% by weight.

5. A solid oral dosage form according to claim 1, wherein the active ingredient is present in an amount ranging from 46 to 60% by weight.

6. A solid oral dosage form according to claim 1, wherein the active ingredient consists entirely of aliskiren, or a pharmaceutically acceptable salt thereof, and is present in an amount ranging from about 75 to about 600 mg of the free base per unit dosage form.

7. A solid oral dosage form according to claim 1, wherein the active ingredient consists entirely of aliskiren, or a pharmaceutically acceptable salt thereof, and is present in an amount ranging from about 75 to about 300 mg of the free base per unit dosage form.

8. A solid oral dosage form according to claim 7, wherein aliskiren is in the form of a hemi-fumarate thereof, and is present in an amount of about 83 mg per unit dosage form.

9. A solid oral dosage form according to claim 8, wherein aliskiren is in the form of a hemi-fumarate thereof, and is present in an amount of about 166 mg per unit dosage form.

10. A solid oral dosage form according to claim 6, wherein aliskiren is in the form of a hemi-fumarate thereof, and is present in an amount of about 332 mg per unit dosage form.

11. A solid oral dosage form according to claim 1 for use in the manufacture of a medicament for the treatment of hypertension.

12. A solid oral dosage form according to claim 1, wherein the active ingredient is present in an amount of more than 46% up to 56% by weight.

13. A solid oral dosage form according to claim 2, wherein the filmcoating material is hydroxypropyl methyl cellulose.

14. A solid oral dosage form according to claim 2 or 13, wherein the film coat further comprises additives selected from pigments, dies, titanium dioxide, iron oxides, talc, and polyethylene glycols 3350, 4000, 6000 and 8000.

15. A solid oral dosage form according to claim 2, wherein the film coat comprises hydroxypropyl methyl cellulose, iron oxide pigments, titanium dioxide, polyethylene glycol, and talc.

16. A solid oral dosage form according to claim 1 comprising
   82.875 mg aliskiren hemifumarate;
   53.625 mg microcrystalline cellulose;
   6 mg polyvinylpyrrolidone;
   24.1 mg crosslinked polyvinylpyrrolidone;
   0.9 mg colloidal silicon dioxide; and
   2.5 mg magnesium stearate.

17. A solid oral dosage form according to claim 1 comprising
   165.75 mg aliskiren hemifumarate;
   107.25 mg microcrystalline cellulose;

12 mg polyvinylpyrrolidone;
48.2 mg crosslinked polyvinylpyrrolidone;
1.8 mg colloidal silicon dioxide; and
5 mg magnesium stearate.

18. A solid oral dosage form according to claim 1 comprising
331.5 mg aliskiren hemifumarate;
214.5 mg microcrystalline cellulose;
24 mg polyvinylpyrrolidone;
96.4 mg crosslinked polyvinylpyrrolidone;
3.6 mg colloidal silicon dioxide; and
10 mg magnesium stearate.

19. A method for the treatment of hypertension, congestive heart failure, angina, myocardial infarction, artherosclerosis, diabetic nephropathy, diabetic cardiac myopathy, renal insufficiency, peripheral vascular disease, left ventricular hypertrophy, cognitive dysfunction, stroke, headache and chronic heart failure which method comprises administering a therapeutically effective amount of a solid oral dosage form according to claim 1 to a patient in need thereof.

20. A process for the manufacture of a solid oral dosage form according to claim 1 comprising:
1) mixing the active ingredient and microcrystalline cellulose, polyvinylpyrrolidone, and crosslinked polyvinylpyrrolidone and granulating said components with a granulation liquid;
2) drying a resulting granulate;
3) mixing the dried granulate with crosslinked polyvinylpyrrolidone, microcrystalline cellulose, colloidal silicon dioxide, and magnesium stearate;
4) compressing a resulting mixture to form a solid oral dosage as a core tablet; and
5) optionally coating a resulting core tablet to give a film-coated tablet.

* * * * *

UNITED STATES PATENT AND TRADEMARK OFFICE
CERTIFICATE OF CORRECTION

| | | |
|---|---|---|
| PATENT NO. | : 8,617,595 B2 | Page 1 of 1 |
| APPLICATION NO. | : 10/590398 | |
| DATED | : December 31, 2013 | |
| INVENTOR(S) | : Rogassi-Dietrich et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 473 days.

Signed and Sealed this
Fourteenth Day of April, 2015

Michelle K. Lee
*Director of the United States Patent and Trademark Office*